United States Patent [19]

Shiotani et al.

[11] Patent Number: 5,892,108

[45] Date of Patent: Apr. 6, 1999

[54] METHOD FOR PACKING WITH CATALYST FOR SYNTHESIS OF UNSATURATED ALDEHYDE AND UNSATURATED CARBOXYLIC ACID

[75] Inventors: Tohru Shiotani; Miezi Sugiyama; Toru Kuroda; Motomu Oh-Kita, all of Otake, Japan

[73] Assignee: Mitsubishi Rayon Co., Ltd., Tokyo, Japan

[21] Appl. No.: 852,162

[22] Filed: May 6, 1997

[30]     Foreign Application Priority Data

May 9, 1996  [JP]  Japan ..................................... 8-137717

[51] Int. Cl.[6] ................................................... C07C 51/16
[52] U.S. Cl. ......................... 562/532; 562/535; 568/479; 502/212; 502/242; 502/304; 502/527
[58] Field of Search ..................................... 502/205, 212, 502/242, 306, 309, 527; 568/479; 562/532, 535

[56]           References Cited

U.S. PATENT DOCUMENTS 3,484,384  12/1969  Kerr et al. ............................... 252/437
4,438,217  3/1984  Takata et al. ............................ 502/205

FOREIGN PATENT DOCUMENTS 62-36739  8/1987  Japan .
62-36740  8/1987  Japan .
4-119901  4/1992  Japan .

Primary Examiner—Shailendra Kumar
Assistant Examiner—Sreeni Padmanabhan
Attorney, Agent, or Firm—Oblon, Spivak, McClelland, Maier & Neustadt, P.C.

[57]           ABSTRACT

A method for packing of catalyst, which comprises mixing, into a shaped catalyst containing at least molybdenum and iron, used in the gas-phase catalytic oxidation of propylene, isobutylene, tert-butyl alcohol or methyl tert-butyl ether with molecular oxygen to synthesize an unsaturated aldehyde and an unsaturated carboxylic acid both corresponding to the raw material used, metal-made Raschig rings as auxiliary packing material having a bulk volume of 0.3–3.5 times that of the shaped catalyst and a packing density of 0.5–1.5 kg/l, and packing the resulting mixture into a fixed bed type reactor; and a process for producing an unsaturated aldehyde and an unsaturated carboxylic acid, which comprises subjecting propylene, isobutylene, tert-butyl alcohol or methyl tert-butyl ether to gas-phase catalytic oxidation using molecular oxygen, in a fixed bed type reactor wherein a catalyst is packed by the above method.

15 Claims, No Drawings

METHOD FOR PACKING WITH CATALYST FOR SYNTHESIS OF UNSATURATED ALDEHYDE AND UNSATURATED CARBOXYLIC ACID

BACKGROUND OF THE INVENTION

1. Field of the Invention

The present invention relates to a method for packing, into a fixed bed type reactor, a catalyst containing at least molybdenum and iron, used in the gas-phase catalytic oxidation of propylene, isobutylene, tert-butyl alcohol (hereinafter abbreviated to TBA) or methyl tert-butyl ether (hereinafter abbreviated to MTBE) with molecular oxygen to synthesize an unsaturated aldehyde and an unsaturated carboxylic acid both corresponding to the raw material used. The present invention relates also to a process for producing an unsaturated aldehyde and an unsaturated carboxylic acid in a reactor wherein a catalyst is packed by the above method.

2. Description of Related Art

Generally in a fixed bed type reactor, there is employed a method for packing of catalyst which comprises dropping, into the reactor from its top, a shaped catalyst or a supported catalyst, used in the gas-phase catalytic oxidation of propylene, isobutylene, TBA or MTBE with molecular oxygen. When, in the catalytic oxidation, a raw material gas is passed through the reactor, a pressure loss appears owing to the packed molded catalyst or supported catalyst and this pressure loss becomes larger owing to the pulverization or disintegration of catalyst brought about by the physical impact which the catalyst receives when dropped.

In the gas-phase catalytic oxidation of propylene, isobutylene, TBA or MTBE using molecular oxygen, the reaction is carried out at a low pressure in order to suppress successive oxidation, whereby an intended unsaturated aldehyde and an intended carboxylic acid both corresponding to the raw material used can be produced at high yields. In carrying out the gas-phase catalytic oxidation on an industrial scale, however, a pressure loss appears and it becomes larger for the reasons mentioned above; therefore, it is difficult to carry out the reaction at a low pressure.

In an attempt to keeping low the pressure loss caused by catalyst, JP-B-62-36739, JP-B-62-36740, etc. disclose a method for keeping low the pressure loss by using a shaped catalyst of appropriately selected shape. Use of a shaped catalyst of appropriately selected shape alone cannot keep the pressure loss sufficiently low, and an effective method for keeping low the pressure loss is being looked for. Further, JP-A-4-119901 discloses mixed use of a reforming catalyst and an auxiliary packing material in the reforming of a hydro-carbon type fuel and shows, in the Examples, a case of using stainless steel-made Raschig rings as an auxiliary packing material. In this case, however, the auxiliary packing material has a bulk volume of about 0.1 time that of the reforming catalyst and, when their mixture is dropped into a reactor from its top, the catalyst and the auxiliary packing material are packed in the reactor in a nonuniformly mixed state. Although an auxiliary packing material has, in an exothermic reaction such as oxidation reaction or the like, a role of diluent capable of preventing the generation of hot spots, the packing of the catalyst and the auxiliary packing material in a nonuniformly mixed state generates hot spots.

SUMMARY OF THE INVENTION

The present invention provides a method for packing of catalyst, employed in the gas-phase catalytic oxidation of propylene, isobutylene, TBA or MTBE using molecular oxygen, which method can lower the pressure loss in the reactor and suppress the generation of hot spots to advantageously synthesize intended products.

The present invention lies in a method for packing of catalyst, which comprises mixing, into a shaped catalyst containing at least molybdenum and iron, used in the gas-phase catalytic oxidation of propylene, isobutylene, tert-butyl alcohol or methyl tert-butyl ether with molecular oxygen to synthesize an unsaturated aldehyde and an unsaturated carboxylic acid both corresponding to the raw material used, metal-made Raschig rings as auxiliary packing material having a bulk volume of 0.3–3.5 times that of the shaped catalyst and a packing density of 0.5–1.5 kg/l, and packing the resulting mixture into a fixed bed type reactor.

The present invention relates also to a process for producing an unsaturated aldehyde and an unsaturated carboxylic acid, which comprises subjecting propylene, isobutylene, tert-butyl alcohol or methyl tert-butyl ether to gas-phase catalytic oxidation using molecular oxygen, in a fixed bed type reactor in which a catalyst is packed by the above method.

PREFERRED EMBODIMENTS OF THE INVENTION

In the present invention, in order to make small the pressure loss appearing in the reactor during the reaction, metal-made Raschig rings as auxiliary packing material having a bulk volume of particular ratio to that of the shaped catalyst used together and a particular packing density is mixed with the catalyst and the resulting mixture is packed into the reactor.

The metal-made Raschig rings used as an auxiliary packing material in the present invention has a bulk volume of preferably 0.3–3.5 times that of the shaped catalyst and/or a packed density of preferably 0.5–1.5 kg/l. The bulk volume is more preferably 0.5–3 times that of the shaped catalyst, further preferably 1–2.06 times. The packing density is more preferably 0.6–1.3 kg/l. Herein, "bulk volume" refers to an apparent volume including any vacant space. When the shaped catalyst and the auxiliary packing material each have a ring shape (hollow cylindrical shape) or a Raschig ring shape, the bulk volumes thereof are each a volume of a cylinder defined by the circumferential side wall. "Packing density" refers to the reciprocal of a volume occupied by 1 kg of an auxiliary packing material in a stainless steel-made reactor of 26 mm (internal diameter) and 5 m (length) when the auxiliary packing material was dropped and packed into the reactor and said volume was calculated from the length of the auxiliary packing material packed in the reactor.

By thus allowing the auxiliary packing material to have a bulk volume of particular range which is not largely different from that of the shaped catalyst, the shaped catalyst can be uniformly diluted and mixed with the auxiliary packing material in a fixed bed type reactor and, as a result, generation of hot spots during reaction can be prevented. Further, by allowing the auxiliary packing material to have a bulk volume of particular range mentioned above, the entering of the shaped catalyst into the vacant space of each metal-made Raschig ring (the auxiliary packing material) can be prevented, whereby the pressure loss in the reactor can be made small. By allowing the packing density to have a particular range mentioned above, there can be made small the pressure loss in the reactor which occurs owing to the pulverization and disintegration of the shaped catalyst in packing of a mixture of the shaped catalyst and the auxiliary packing material. The pressure loss can be minimized when the catalyst packing method of the present invention is employed particularly in packing of, for example, a ring-shaped catalyst which has relatively low physical strengths and which tends to cause pulverization and disintegration in the course of packing into a reactor.

The amount of the metal-made Raschig rings to be mixed with the catalyst is preferably 1–300 parts by weight, more preferably 10–50 parts by weight per 100 parts by weight of the catalyst.

The outer diameter of each metal-made Raschig ring is preferably 2.5–13.0 mm, more preferably 3.0–8.0 mm. The length of each metal-made Raschig ring is preferably 2.5–13.0 mm, more preferably 3.0–8.0 mm. Metal-made Raschig rings which are dented inwardly or protruded outwardly at some portions of the side wall, are particularly preferred because they can greatly reduce the pressure loss in reactor.

The material for metal-made Raschig rings can be any material as long as it does not hinder the gas-phase catalytic oxidation of propylene, isobutylene, TBA or MTBE using molecular oxygen. It includes, for example, carbon steel, stainless steel and titanium. Stainless steel is preferred in view of the mechanical strengths when used industrially, the handleability, the cost, etc.

The catalyst used in the present invention is a catalyst used in the gas-phase catalytic oxidation of propylene, isobutylene, TBA or MTBE with molecular oxygen to synthesize an unsaturated aldehyde and an unsaturated carboxylic acid both corresponding to the raw material used. It contains at least molybdenum and iron as the constituent elements.

The molybdenum- and iron-containing catalyst is preferably an oxide catalyst having a composition represented by the following general formula:

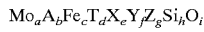

$Mo_aA_bFe_cT_dX_eY_fZ_gSi_hO_i$ (wherein Mo, Fe, Si and O represent molybdenum, iron, silicon and oxygen, respectively; A represents at least one element selected from the group consisting of bismuth and tellurium; T represents at least one element selected from the group consisting of cobalt and nickel; X represents at least one element selected from the group consisting of chromium, lead, manganese, calcium, magnesium, niobium, silver, barium, tin, tantalum and zinc; Y represents at least one element selected from the group consisting of phosphorus, boron, sulfur, selenium, cerium, tungsten, antimony and titanium; Z represents at least one element selected from the group consisting of lithium, sodium, potassium, rubidium, cesium and thallium; a, b, c, d, e, f, g, h and i represent the atomic ratios of the individual elements; when a is 12, b=0.01–5, c=0.01–5, d=0–12, e=0–10, f=0–8, g=0.001–2 and h=0–20, and i is the number of oxygen atoms required to satisfy the valencies of the individual components).

As to the process for producing the catalyst used in the present invention, there is no particular restriction. One of conventional well-known processes such as evaporation to dryness, precipitation, oxide mixing and the like can be used unless it invites serious nonuniformity of components in the produced catalyst. The raw material for each catalyst component can be an oxide, a nitrate, a carbonate, an ammonium salt, a hydroxide or the like of each catalyst component, and the raw materials for individual catalyst components can be used in an appropriate combination.

The catalyst containing at least molybdenum and iron, used in the present invention may be a shaped catalyst or a supported catalyst. Regarding the shaped catalyst, there is no restriction as to the shape, and there can be used a catalyst having a spherical shape, a cylindrical shape, a starlike shape or other shape, which is produced by ordinarily used compression tabletting machines, extrusion molding machines, tumbling granulators or the like.

When a supported catalyst is used, there is no restriction as to the kind of the carrier used therein. A carrier such as silica, alumina, silica-alumina, magnesia, titania or the like can be used. There is no restriction, either, as to the shape of the carrier, and a spherical shape, a cylindrical shape, a plate-like shape or the like can be mentioned.

The gas-phase catalytic oxidation reaction according to the present invention is carried out using propylene, isobutylene, TBA or MTBE (a raw material) and molecular oxygen in the presence of the above-mentioned catalyst. The molar ratio of propylene, isobutylene, TBA or MTBE to oxygen is preferably 1:0.5–3. Use of air as an oxygen source is economical, but air enriched with pure oxygen can be used when necessary. The reaction pressure can vary from normal pressure to several atmospheres. The reaction temperature can be selected in the range of 250°–450° C.

The present invention is described below more specifically by way of Examples and Comparative Examples. In the Examples and Comparative Examples, "parts" refer to parts by weight. The analyses of raw materials and products were made by gas chromatography. In the Examples and Comparative Examples, the conversion of raw material (propylene, isobutylene, TBA or MTBE), the selectivities of unsaturated aldehyde formed and unsaturated carboxylic acid formed, and the pressure loss in reactor are defined as follows.

Conversion of raw material (%) =

(moles of raw material reacted) ÷

(moles of raw material fed) × 100

Selectivity of unsaturated aldehyde (%) =

(moles of unsaturated aldehyde formed) ÷

(moles of raw material reacted) × 100

Selectivity of unsaturated carboxylic acid (%) =

(moles of unsaturated carboxylic acid formed) ÷

(moles of raw material reacted) × 100

Pressure loss (%) = 100 − [gas pressure (kg/cm$^2$) at reactor outlet] ÷

[gas pressure (kg/cm$^2$) at reactor inlet] × 100

EXAMPLE 1

To 1,000 parts of water were added 500 parts of ammonium paramolybdenate, 6.2 parts of ammonium paratungstate and 1.4 parts of potassium nitrate, followed by heating with stirring (solution A).

Separately, 41.9 parts of 60% nitric acid was added to 600 parts of water, and they were made uniform. Thereto was added 103.0 parts of bismuth nitrate, and they were made into a solution. To the solution were added 125.0 parts of ferric nitrate, 425.8 parts of cobalt nitrate and 21.1 parts of zinc nitrate in this order. Then, 400 parts of water was added to obtain a solution (solution B).

The solution B was added to the solution A to obtain a slurry. Thereto was added 41.3 parts of antimony trioxide, and the mixture was heated with stirring to vaporize most of the water contained therein.

The resulting cake-like material was dried at 130° C. and then subjected to calcining in an air atmosphere at 300° C. for 1 hour. The resulting material was ground. The ground material was molded into rings of 5 mm in outer diameter, 2 mm in inner diameter and 5 mm in average length by the use of a dry compression tabletting machine. The rings were subjected to calcining at 520° C. for 3 hours to obtain a shaped catalyst. The shaped catalyst had the following elemental composition excluding oxygen (the same applies hereinafter).

$$Mo_{12}W_{0.1}Bi_{0.9}Fe_{1.3}Sb_{1.2}Co_{6.2}Zn_{0.3}K_{0.06}$$

1,200 g of the shaped catalyst was uniformly m mixed with 500 g of SUS 304-made Raschig rings having an outer diameter of 5 mm, a difference between outer diameter and inner diameter, of 0.4 mm, a length of 5 mm and a packing density of 1.1 kg/l (the bulk volume ratio of a metal-make Raschig ring to a shaped catalyst was 1). The resulting mixture was dropped, for packing, into a stainless steel-made reactor having an inner diameter of 26 mm and a length of 5 m. Then, through the reactor was passed 2,500 Nl/h of a mixed raw material gas consisting of 5% of propylene, 12% of oxygen, 10% of steam and 73% of nitrogen (all % by volume) so that the reactor outlet pressure became 0.7 kg/cm$^2$, and a reaction was carried out at 305° C. As a result, the conversion of propylene was 99.0%; the selectivity of acrolein was 87.0%; and the selectivity of acrylic acid was 5.9%. The pressure loss was 30.8%.

EXAMPLE 2

1,200 g of a ground material obtained in the same manner as in Example 1 was mixed with 360 parts of water and 36 parts of methyl cellulose. They were kneaded and extrusion-molded into rings having an outer diameter of 8 mm, an inner diameter of 4 mm and an average length of 5 mm. The rings were dried in a hot-air dryer at 100° C. for 1 hour and then subjected to calcining at 520° C. for 3 hours to obtain a shaped catalyst. 1,200 g of the shaped catalyst was uniformly mixed with 500 g of SUS 304-made Raschig rings having an outer diameter of 8 mm, a difference between outer diameter and inner diameter, of 0.4 mm, a length of 8 mm and a packing density of 1.1 kg/l (the bulk volume ratio of a metal-made Raschig ring to a shaped catalyst was 1.6). Using the resulting mixture, catalyst packing and a reaction were carried out under the same conditions as in Example 1. As a result, the conversion of propylene was 98.9%; the selectivity of acrolein was 86.8%; and the selectivity of acrylic acid was 5.9%. The pressure loss was 25.6%.

Comparative Example 1

Catalyst production, catalyst packing and a reaction were carried out in the same manner as in Example 1 except that the SUS 304-made Raschig rings were changed to ceramic balls having a packing density of 1.22 kg/l and a diameter of 7 mm (the bulk volume ratio of a ceramic ball to a shaped catalyst was 1.83). As a result, the conversion of propylene was 99.0%; the selectivity of acrolein was 86.3%; and the selectivity of acrylic acid was 5.2%. The pressure loss was 51.1%.

Comparative Example 2

Catalyst production, catalyst packing and a reaction were carried out in the same manner as in Example 1 except that there were used, as an auxiliary packing material, SUS 304-made Raschig rings having an outer diameter of 10 mm, a difference between outer diameter and inner diameter, of 0.4 mm, a length of 10 mm and a packing density of 0.6 kg/l (the bulk volume ratio of a metal-made Raschig ring to a shaped catalyst was 8). As a result, the conversion of propylene was 99.1%; the selectivity of acrolein was 85.5%; and the selectivity of acrylic acid was 6.1%. However, there was generation of hot spots and the dilution effect for catalyst was small. The pressure loss was 39.8%.

Comparative Example 3

Catalyst production, catalyst packing and a reaction were carried out in the same manner as in Example 1 except that the SUS 304-made Raschig rings were changed to ceramic Raschig rings having an outer diameter of 6 mm, a difference between outer diameter and inner diameter, of 2.0 mm, a length of 6 mm and a packing density of 1.26 kg/l (the bulk volume ratio of a ceramic Raschig ring to a shaped catalyst was 1.73). As a result, the conversion of propylene was 99.0%; the selectivity of acrolein was 85.6%; and the selectivity of acrylic acid was 5.4%. The pressure loss was 48.6%.

EXAMPLE 3

42 parts of 60% nitric acid was added to 400 parts of water, and they were made into a uniform solution. Therein was dissolved 68.7 parts of bismuth nitrate. Thereto were added 102.9 parts of nickel nitrate and 24.1 parts of antimony trioxide in this order. The mixture was dissolved and decomposed. Thereto was added 165 parts of 28% ammonia water to obtain a blue solution containing a white precipitate. The solution was heated with stirring to vaporize most of the water contained therein. The resulting slurry material was dried at 120° C. for 16 hours, then subjected to a heat treatment at 750° C. for 2 hours, and finely ground to obtain a fine powder of a bismuth-nickel-antimony compound.

To 1,000 parts of water were added 500 parts of ammonium paramolybdenate, 12.3 parts of ammonium paratungstate and 23.0 parts of cesium nitrate. They were heated with stirring (solution A). Separately, to 700 parts of water were added 230.8 parts of ferric nitrate, 418.9 parts of cobalt nitrate and 60.5 parts of magnesium nitrate in this order, and they were made into a solution (solution B). The solution B was added to the solution A to obtain a slurry. To the slurry were added 425.5 parts of 20% silica sol and the above-obtained fine powder of a bismuth-nickel-antimony compound, and the mixture was heated with stirring to vaporize most of the water contained therein.

The resulting cake-like material was dried at 130° C. and then subjected to calcining in an air atmosphere at 300° C. for 1 hour. The resulting material was ground. The ground material was molded into rings of 5 mm in outer diameter, 2 mm in inner diameter and 5 mm in average length by the use of a dry compression tabletting machine. The rings were subjected to calcining at 520° C. for 3 hours to obtain a shaped catalyst. The shaped catalyst had the following elemental composition.

$$Mo_{12}W_{0.2}Bi_{0.6}Fe_{2.4}Sb_{0.7}Ni_{1.5}Co_{6.1}Mg_{1.0}Cs_{0.5}Si_{6.0}$$

1,200 g of the shaped catalyst was uniformly mixed with 500 g of SUS 304-made Raschig rings having an outer diameter of 5 mm, a difference between outer diameter and inner diameter, of 0.4 mm, a length of 5 mm and a packing density of 1.1 kg/l (the bulk volume ratio of a Raschig ring to a shaped catalyst was 1). The resulting mixture was dropped, for packing, into a stainless steel-made reactor having an inner diameter of 26 mm and a length of 5 m. Then, through the reactor was passed 2,500 Nl/h of a mixed raw material gas consisting of 5% of isobutylene, 12% of oxygen, 10% of steam and 73% of nitrogen (all % by volume) so that the reactor outlet pressure became 0.7 kg/cm$^2$, and a reaction was carried out at 340° C. As a result, the conversion of isobutylene was 97.5%; the selectivity of methacrolein was 87.4%; and the selectivity of methacrylic acid was 3.6%. The pressure loss was 30.1%.

Comparative Example 4

Catalyst production, catalyst packing and a reaction were conducted in the same manner as in Example 3 except that there were used, as an auxiliary packing material, SUS 304-made Raschig rings having an outer diameter of 5 mm, a difference between outer diameter and inner diameter, of 0.8 mm, a length of 5 mm and a packing density of 2.0 kg/l (the bulk volume ratio of a Raschig ring to a shaped catalyst was 1). As a result, the conversion of isobutylene was 96.6%; the selectivity of methacrolein was 86.0%; and the selectivity of methacrylic acid was 3.1%. The pressure loss was 50.2%.

EXAMPLE 4

1,200 g of a ground material obtained in the same manner as in Example 3 was mixed with 360 parts of water and 36 parts of methyl cellulose. They were kneaded and extrusion-molded into rings having an outer diameter of 6 mm, an inner diameter of 3 mm and an average length of 5 mm. The rings were dried in a hot-air dryer at 100° C. for 1 hour and then subjected to calcining at 520° C. for 3 hours to obtain a shaped catalyst. 1,200 g of the shaped catalyst was uniformly mixed with 500 g of SUS 304-made Raschig rings having an outer diameter of 6 mm, a difference between outer diameter and inner diameter, of 0.4 mm, a length of 6 mm and a packing density of 1.0 kg/l (the bulk volume ratio of a Raschig ring to a shaped catalyst was 1.2). Using the resulting mixture, catalyst packing and a reaction were carried out under the same conditions as in Example 3. As a result, the conversion of isobutylene was 97.4%; the selectivity of methacrolein was 87.5%; and the selectivity of acrylic acid was 3.5%. The pressure loss was 26.3%.

Comparative Example 5

Catalyst production, catalyst packing and a reaction were carried out in the same manner as in Example 3 except that the SUS 304-made Raschig rings were changed to ceramic balls having a packing density of 1.22 kg/l and a diameter of 7 mm (the bulk volume ratio of a ceramic ball to a shaped catalyst was 1.83). As a result, the conversion of isobutylene was 96.3%; the selectivity of methacrolein was 86.4%; and the selectivity of methacrylic acid was 2.5%. The pressure loss was 51.3%.

Comparative Example 6

Catalyst production, catalyst packing and a reaction were carried out in the same manner as in Example 3 except that the SUS 304-made Raschig rings were changed to ceramic Raschig rings having an outer diameter of 6 mm, a difference between outer diameter and inner diameter, of 2.0 mm, a length of 6 mm and a packing density of 1.26 kg/l (the bulk volume ratio of a ceramic Raschig ring to a shaped catalyst was 1.73). As a result, the conversion of isobutylene was 96.4%; the selectivity of methacrolein was 86.5%; and the selectivity of methacrylic acid was 2.6%. The pressure loss was 47.1%.

EXAMPLE 5

To 1,000 parts of pure water were added 500 parts of ammonium paramolybdenate and 9.2 parts of cesium nitrate. They were heated to obtain a solution. Thereto was added a solution of 209.8 parts of ferric nitrate, 625.3 parts of lead nitrate and 162.6 parts of telluric acid dissolved in 3,000 parts of pure water. To the resulting slurry were added 178.9 parts of antimony trioxide and 709.0 parts of 30% silica sol. The mixture was stirred to vaporize most of the water contained therein.

The resulting cake-like material was dried at 130° C. and then subjected to calcining in an air atmosphere at 300° C. for 1 hour. The resulting material was ground. The ground material was molded into rings of 5 mm in outer diameter, 2 mm in inner diameter and 5 mm in average length by the use of a dry compression tabletting machine. The rings were subjected to calcining at 500° C. for 3 hours to obtain a shaped catalyst. The shaped catalyst had the following elemental composition.

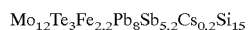

$$Mo_{12}Te_3Fe_{2.2}Pb_8Sb_{5.2}Cs_{0.2}Si_{15}$$

1,200 g of the shaped catalyst was uniformly mixed with 500 g of SUS 304-made Raschig rings having an outer diameter of 5 mm, a difference between outer diameter and inner diameter, of 0.4 mm, a length of 5 mm and a packing density of 1.1 kg/l (the bulk volume ratio of a Raschig ring to a shaped catalyst was 1). The resulting mixture was dropped, for packing, into a stainless steel-made reactor having an inner diameter of 26 mm and a length of 5 m. Then, through the reactor was passed 2,500 Nl/h of a mixed raw material gas consisting of 5% of isobutylene, 12% of oxygen, 10% of steam and 73% of nitrogen (all % by volume) so that the reactor outlet pressure became 0.7 kg/cm$^2$, and a reaction was carried out at 360° C. As a result, the conversion of isobutylene was 94.7%; the selectivity of methacrolein was 86.6%; and the selectivity of acrylic acid was 2.1%. The pressure loss was 31.0%.

EXAMPLE 6

1,200 parts of a ground material obtained in the same manner as in Example 5 was mixed with water to obtain a slurry. The slurry was gradually coated on 2,400 parts of a spherical alumina carrier having a diameter of 4.5 mm which was being fluidized with heating (the bulk volume ratio of a carrier to a shaped catalyst obtained was 2.06). The coated carrier was subjected to calcining at 500° C. for 3 hours to obtain a supported catalyst. Using the catalyst, catalyst packing and a reaction were carried out under the same conditions as in Example 5. As a result, the conversion of isobutylene was 94.9%; the selectivity of methacrolein was 86.8%; and the selectivity of methacrylic acid was 2.0%. The pressure loss was 34.9%.

Comparative Example 7

Catalyst packing and a reaction were carried out under the same conditions as in Example 5 except that no SUS 304-made Raschig rings were added. As a result, too high a reaction heat generated, making it impossible to continue the reaction.

EXAMPLE 7

Catalyst packing and a reaction were carried out under the same conditions as in Example 3 except that the raw material was changed to TBA. As a result, the conversion of TBA was 100%; the selectivity of methacrolein was 85.3%; and the selectivity of methacrylic acid was 2.4%. The pressure loss was 30.7%.

Comparative Example 8

Catalyst packing and a reaction were carried out under the same conditions as in Comparative Example 3 except that the catalyst obtained in Example 3 was used and the raw material was changed to TBA. As a result, the conversion of TBA was 100%; the selectivity of methacrolein was 82.8%; and the selectivity of methacrylic acid was 1.8%. The pressure loss was 51.9%.

The present application is based on Japanese Patent Application No. 8-137717 filed on May 9, 1996, the contents of which are incorporated herein in its entirety by reference.

We claim:

1. A method for packing of catalyst, which comprises mixing, into a shaped catalyst containing at least molybdenum and iron, used in the gas-phase catalytic oxidation of propylene, isobutylene, tert-butyl alcohol or methyl tert-butyl ether with molecular oxygen to synthesize an unsaturated aldehyde and an unsaturated carboxylic acid both corresponding to the raw material used, metal-made Raschig rings as auxiliary packing material having a bulk volume of 0.3–3.5 times that of the shaped catalyst and a packing density of 0.5–1.5 kg/l, and packing the resulting mixture into a fixed bed type reactor.

2. A method according to claim 1, wherein the metal-made Raschig rings are used in an amount of 1–300 parts by weight per 110 parts by weight of the catalyst.

3. A method according to claim 1, wherein the metal-made Raschig rings have an outer diameter of 2.5–13.0 mm.

4. A method according to claim 3, wherein the metal-made Raschig rings have a length of 2.5–13.0 mm.

5. A method according to claim 1, wherein the metal-made Raschig rings are made of stainless steel.

6. A method according to claim 3, wherein the metal-made Raschig rings are made of stainless steel.

7. A method according to claim 4, wherein the metal-made Raschig rings are made of stainless steel.

8. A method according to claim 1, wherein the catalyst is an oxide catalyst having a composition represented by the following general formula:

$$Mo_aA_bFe_cT_dX_eY_fZ_gSi_hO_i$$

(wherein Mo, Fe, Si and O represent molybdenum, iron, silicon and oxygen, respectively; A represents at least one element selected from the group consisting of bismuth and tellurium; T represents at least one element selected from the group consisting of cobalt and nickel; X represents at least one element selected from the group consisting of chromium, lead, manganese, calcium, magnesium, niobium, silver, barium, tin, tantalum and zinc; Y represents at least one element selected from the group consisting of phosphorus, boron, sulfur, selenium, cerium, tungsten, antimony and titanium; Z represents at least one element selected from the group consisting of lithium, sodium, potassium, rubidium, cesium and thallium; a, b, c, d, e, f, g, h and i represent the atomic ratios of the individual elements; when a is 12, b=0.01–5, c=0.01–5, d=0–12, e=0–10, f=0–8, g=0.001–2 and h=0–20, and i is the atomic ratio of oxygen atoms required to satisfy the valencies of the above individual components).

9. A method according to claim 3, wherein the catalyst is an oxide catalyst having a composition represented by the following general formula:

$$Mo_aA_bFe_cT_dX_eY_fZ_gSi_hO_i$$

(wherein Mo, Fe, Si and O represent molybdenum, iron, silicon and oxygen, respectively; A represents at least one element selected from the group consisting of bismuth and tellurium; T represents at least one element selected from the group consisting of cobalt and nickel; X represents at least one element selected from the group consisting of chromium, lead, manganese, calcium, magnesium, niobium, silver, barium, tin, tantalum and zinc; Y represents at least one element selected from the group consisting of phosphorus, boron, sulfur, selenium, cerium, tungsten, antimony and titanium; Z represents at least one element selected from the group consisting of lithium, sodium, potassium, rubidium, cesium and thallium; a, b, c, d, e, f, g, h and i represent the atomic ratios of the individual elements; when a is 12, b=0.01–5, c=0.01–5, d=0–12, e=0–10, f=0–8, g=0.001–2 and h=0–20, and i is the atomic ratio of oxygen atoms required to satisfy the valencies of the above individual components).

10. A method according to claim 4, wherein the catalyst is an oxide catalyst having a composition represented by the following general formula:

$$Mo_aA_bFe_cT_dX_eY_fZ_gSi_hO_i$$

(wherein Mo, Fe, Si and O represent molybdenum, iron, silicon and oxygen, respectively; A represents at least one element selected from the group consisting of bismuth and tellurium; T represents at least one element selected from the group consisting of cobalt and nickel; X represents at least one element selected from the group consisting of chromium, lead, manganese, calcium, magnesium, niobium, silver, barium, tin, tantalum and zinc; Y represents at least one element selected from the group consisting of phosphorus, boron, sulfur, selenium, cerium, tungsten, antimony and titanium; Z represents at least one element selected from the group consisting of lithium, sodium, potassium, rubidium, cesium and thallium; a, b, c, d, e, f, g, h and i represent the atomic ratios of the individual elements; when a is 12, b=0.01–5, c=0.01–5, d=0–12, e=0–10, f=0–8, g=0.001–2 and h=0–20, and i is the atomic ratio of oxygen atoms required to satisfy the valencies of the above individual components).

11. A process for producing an unsaturated aldehyde and an unsaturated carboxylic acid, which comprises subjecting propylene, isobutylene, tert-butyl alcohol or methyl tert-butyl ether to gas-phase catalytic oxidation using molecular oxygen, in a fixed bed type reactor packed with a mixture obtained by mixing, into a shaped catalyst containing at least molybdenum and iron, used in the gas-phase catalytic oxidation of propylene, isobutylene, tert-butyl alcohol or methyl tert-butyl ether with molecular oxygen to synthesize an unsaturated aldehyde and an unsaturated carboxylic acid both corresponding to the raw material used, metal-made Raschig rings as auxiliary packing material having a bulk volume of 0.3–3.5 times that of the shaped catalyst and a packing density of 0.5–1.5 kg/l.

12. A method according to claim 1, wherein the metal-made Raschig rings a bulk volume of 0.5–3 times that of the shaped catalyst.

13. A method according to claim 12, wherein said bulk volume ranges from 1–2.06.

14. A method according to claim 1, wherein said packing density of the metal-made Raschig rings ranges from 0.6 to 1.3 kg/l.

15. A method according to claim 3, wherein said outer diameter ranges from 3.0–8.0 mm.

* * * * *